United States Patent
Li et al.

(10) Patent No.: US 9,538,790 B2
(45) Date of Patent: Jan. 10, 2017

(54) ATOMIZING DEVICE AND ELECTRONIC CIGARETTE HAVING SAME

(71) Applicant: Shenzhen First Union Technology Co., Ltd., Shenzhen (CN)

(72) Inventors: Yonghai Li, Shenzhen (CN); Zhongli Xu, Shenzhen (CN); Yindeng Deng, Shenzhen (CN); Yunping Zhong, Shenzhen (CN)

(73) Assignee: SHENZHEN FIRST UNION TECHNOLOGY CO., LTD., Shenzhen (CN)

( * ) Notice: Subject to any disclaimer, the term of this patent is extended or adjusted under 35 U.S.C. 154(b) by 330 days.

(21) Appl. No.: 14/189,754

(22) Filed: Feb. 25, 2014

(65) Prior Publication Data

US 2014/0334803 A1  Nov. 13, 2014

(30) Foreign Application Priority Data

May 7, 2013 (CN) .................... 2013 2 0245279 U (51) Int. Cl.
*A24F 47/00* (2006.01)
*A61M 15/06* (2006.01)
*H05B 3/03* (2006.01)

(52) U.S. Cl.
CPC ............ *A24F 47/008* (2013.01); *A61M 15/06* (2013.01); *H05B 3/03* (2013.01); *A61M 2205/8206* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,131,599 B2* | 11/2006 | Katase | .................. | A61M 15/02 128/200.14 |
| 9,226,525 B2* | 1/2016 | Liu | ........................ | A24F 47/008 |
| 2006/0196518 A1* | 9/2006 | Hon | ....................... | A24F 47/002 131/360 |
| 2012/0230659 A1* | 9/2012 | Goodman | ............... | F22B 1/282 392/395 |
| 2013/0139833 A1* | 6/2013 | Hon | ....................... | A24F 47/008 131/273 |
| 2013/0192617 A1* | 8/2013 | Thompson | ............ | A24F 47/008 131/329 |

* cited by examiner

*Primary Examiner* — Dana Ross
*Assistant Examiner* — Renee LaRose
(74) *Attorney, Agent, or Firm* — Hamre, Schumann, Mueller & Larson, P.C.

(57) ABSTRACT

An atomizing device includes an atomizing sleeve, an air pipe received in the atomizing sleeve, an annular space being formed between the air pipe and the atomizing sleeve for containing a tobacco oil, an oil obstructing ring located at an end of the air pipe, the oil obstructing ring having an oil hole, an atomizing assembly positioned under the oil obstructing ring, a screw sleeve and an electrode respectively electrically connected to the atomizing assembly; and a flexible membrane having an inner wall attached to the electrode, and an outer wall in contact with an inner wall of the screw sleeve. The flexible membrane is capable of deformable to form an air space between the outer wall of the flexible membrane and the inner wall of the screw sleeve. An electronic cigarette using the atomizing device is also provided.

10 Claims, 8 Drawing Sheets

ATOMIZING DEVICE AND ELECTRONIC CIGARETTE HAVING SAME

BACKGROUND

1. Technical Field

The present invention relates to atomizing devices, and particularly to an atomizing device and an electronic cigarette having the atomizing device.

2. Description of Related Art

Electronic cigarettes are similar to conventional cigarettes in appearance and taste, but less harmful to human's health, such that electronic cigarettes are widely used for helping people to quit smoke. Atomizing devices are key components of electronic cigarettes. A typical atomizing device includes a tobacco oil reserving space and an atomizing assembly. The atomizing assembly has a porous body extending into the tobacco oil reserving space to get the tobacco oil, and the tobacco oil is also sealed by the porous body. However, by this configuration, the tobacco oil may leak out of the atomizing device.

What is needed, therefore, is an atomizing device and an electronic cigarette which can overcome the above shortcomings.

BRIEF DESCRIPTION OF THE DRAWINGS

Many aspects of the present atomizing device and electronic cigarette can be better understood with reference to the following drawings. The components in the drawings are not necessarily drawn to scale, the emphasis instead being placed upon clearly illustrating the principles of the present atomizing device and electronic cigarette. Moreover, in the drawings, like reference numerals designate corresponding parts throughout the several views.

DETAILED DESCRIPTION

Embodiments of the present atomizing device and electronic cigarette will now be described in detail below and with references to the drawings.

Figure 1:
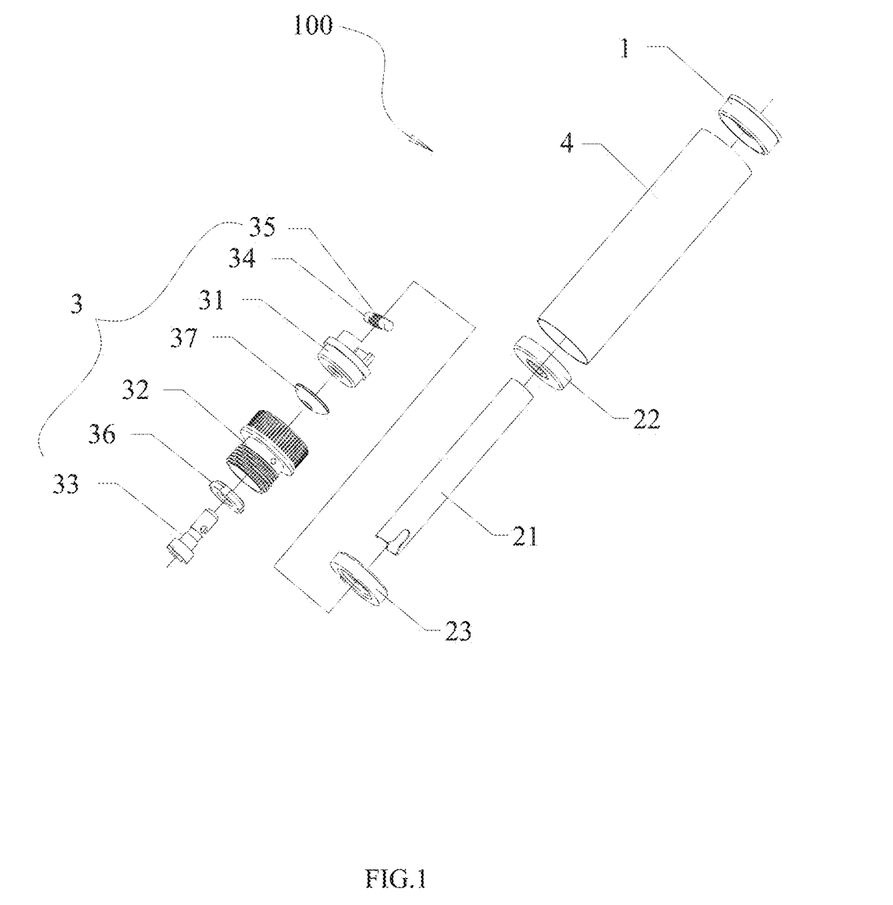
FIG. 1 is a schematic exploded view of an atomizing device of an electronic cigarette in accordance with a first embodiment.
Figure 2:
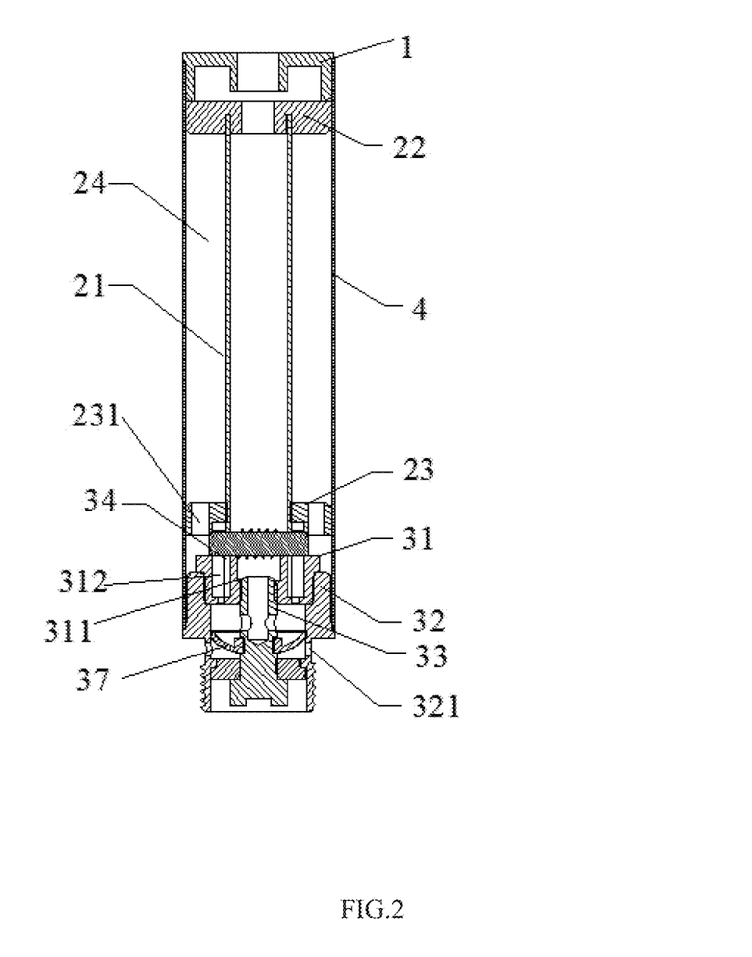
FIG. 2 is an assembled cross sectional view of the atomizing device of FIG. 1.

Referring to FIGS. 1-2, an atomizing device 100 in accordance with a first embodiment is provided. The atomizing device 100 includes a mouthpiece 1, an atomizing sleeve 4, an atomizing assembly 3, an air pipe 21, an upper oil obstructing ring 22 and a lower oil obstructing ring 23. The atomizing sleeve 4 receives all of the elements therein.

The upper oil obstructing ring 22 and the lower oil obstructing ring 23 are located at opposite ends of the air pipe 21. The lower oil obstructing ring 23 has an oil hole 231. An annular space 24 is formed between the atomizing sleeve 4 and the air pipe 21 for containing a tobacco oil.

The atomizing assembly 3 is located under the lower oil obstructing ring 22, and includes a support 31, a screw sleeve 32, a tubular electrode 33, a porous body 34, a heating coil 35, an insulated ring 36 and a flexible membrane 37. The screw sleeve 32 has an outer screw, and two orifices 321 formed in a wall of the screw sleeve 32 for facilitating air enters the atomizing device 100. The support 31 includes a central through hole 311 and two guiding holes 312 formed therein. The porous body 34 is positioned between the lower oil obstructing ring 22 and the support 31, and gets oil from the oil holes 231 from the lower oil obstructing ring 22. The heating coil 35 wraps around the porous body 34, and two ends of the heating coil 35 extend through the respective guiding holes 312 of the support 31 to be electrically connected to the screw sleeve 32 and the tubular electrode 33.

Figure 3:
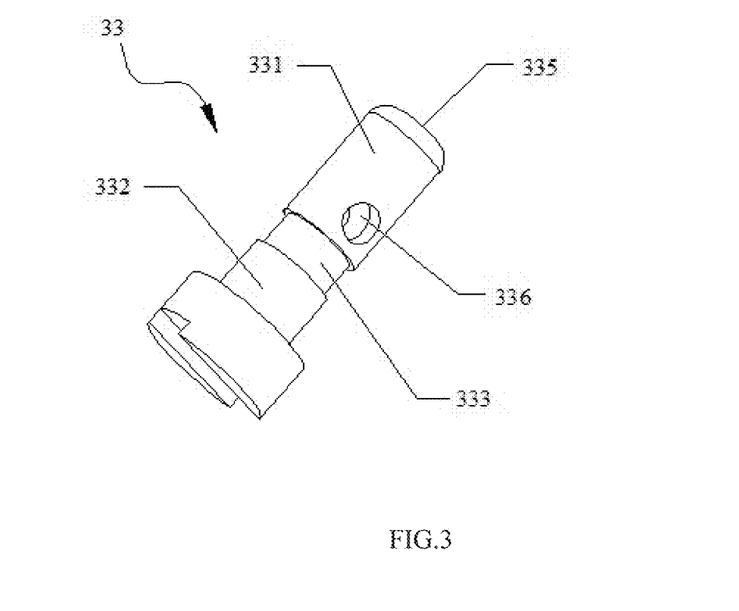
FIG. 3 is a schematic isometric view of a tubular electrode used in the first embodiment.

Referring also to FIG. 3, the tubular electrode 33 includes a front portion 331, a middle portion 333, and a distal portion 332. The middle portion 333 is recessed relative to both of the front portion 331 and the distal portion 332. The front portion 331 has an inner hole 335 exposed to the support 31, and has two orifices 336 formed in a wall and in communication with the inner hole 335. The front portion 331 is received in the central through hole 311 of the support 31. The distal portion 332 is received in the screw sleeve 32 with an insulated ring 36 located between the tubular electrode 33 and the screw sleeve 32.

Figure 4:
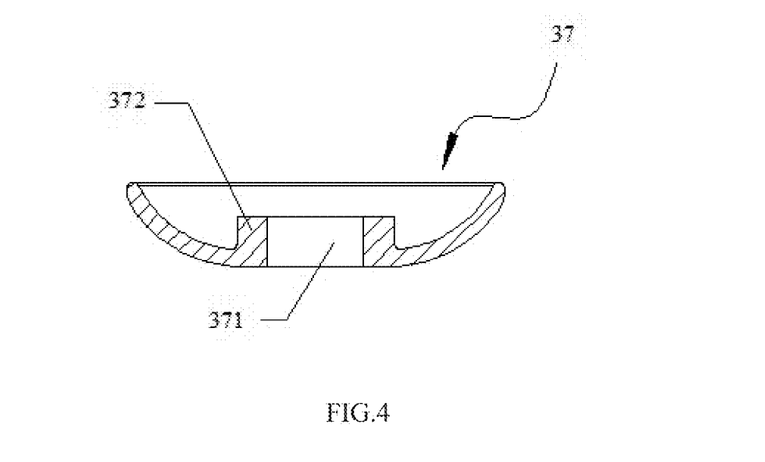
FIG. 4 is a schematic cross sectional view of a flexible membrane used in the first embodiment.

Referring also to FIG. 4, the flexible membrane 37 is in a bowl shape, and includes a protrusion 372 formed at a bottom thereof, and a through hole 371 formed in the protrusion 372. The flexible membrane 37 is made of a silicon dioxide. The protrusion 372 engages with the middle portion 333 of the tubular electrode 33 with the tubular electrode 33 extending through the through hole 371, and an edge of the flexible membrane 37 is in contact with an inner wall of the screw sleeve 32. By this configuration, a top air chamber and a bottom air chamber are formed in the screw sleeve 32 by the flexible membrane 37. A concave inner surface of the bowl-shaped flexible membrane 37 faces toward the top air chamber, and a convex outer surface of the bowl-shaped flexible membrane 37 faces towards the bottom air chamber.

Figure 9:
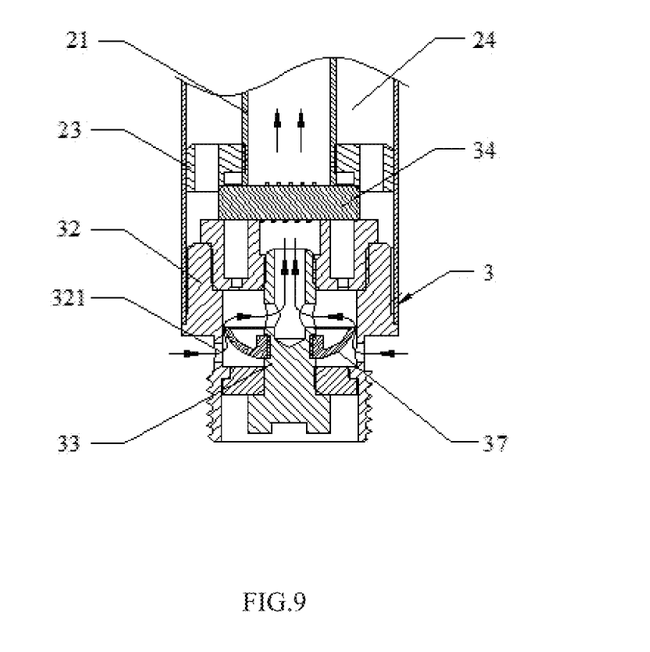
FIG. 9 shows an air flow in the atomizing device of one of the above embodiments.

In a suction state, the air pressure of the top air chamber would be less than that of the bottom air chamber, the flexible membrane 37 then deforms toward the top air chamber, thus an air space is formed between the edge of the flexible membrane 37 and the inner wall of the screw sleeve 32 for facilitating air flow in the atomizing device 100, and the orifices 336 and the inner hole 335 of the tubular electrode 33 cooperatively form an air passage between the screw sleeve 32 and the air pipe 21 (see arrows in FIG. 9). In other states, the flexible membrane 37 contacts the tubular electrode 33 and the screw sleeve 32, thus oil from the atomizing device 100 would not leak out.

Figure 5:
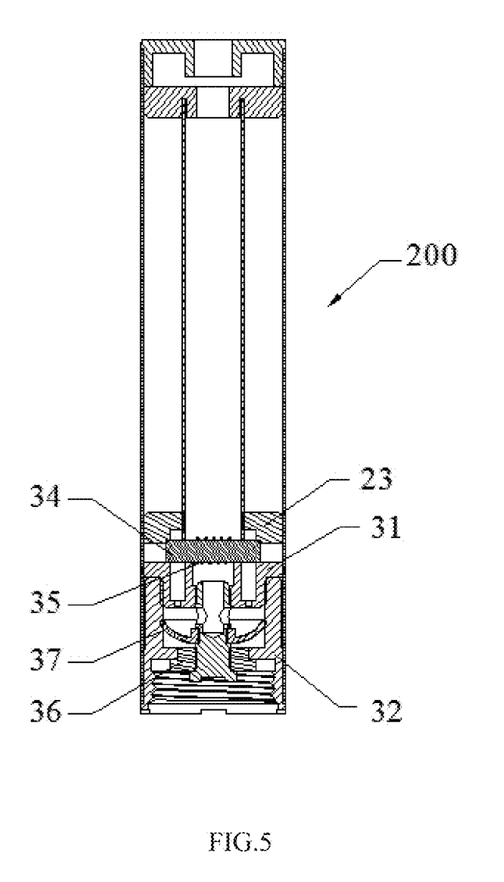
FIG. 5 is a schematic cross sectional view of the atomizing device of an electronic cigarette in accordance with a second embodiment.
Figure 6:
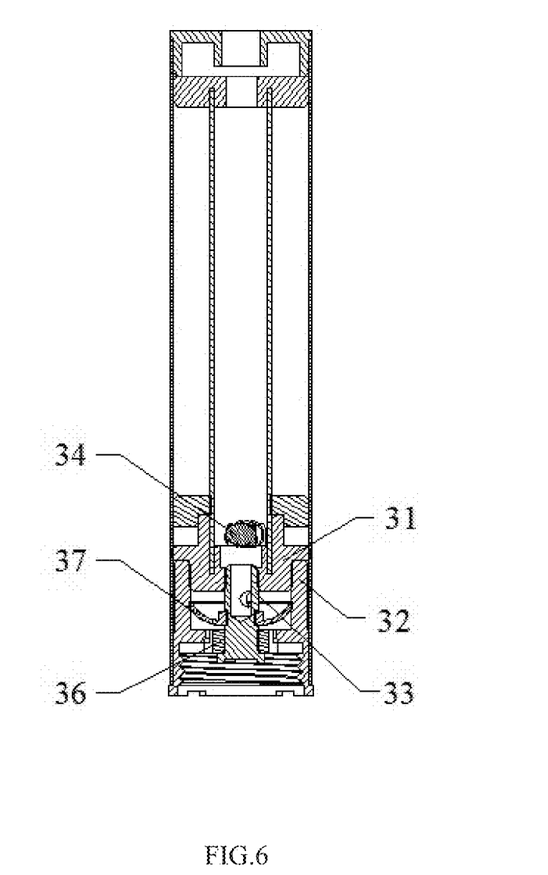
FIG. 6 is similar to FIG. 5, but viewed from another perpendicular angle.

Referring to FIGS. 5 and 6, an atomizing device 200 in accordance with a second embodiment is provided. The atomizing device 200 is essentially similar to the atomizing device 100, however, the screw sleeve 32 has an inner screw.

Figure 7:
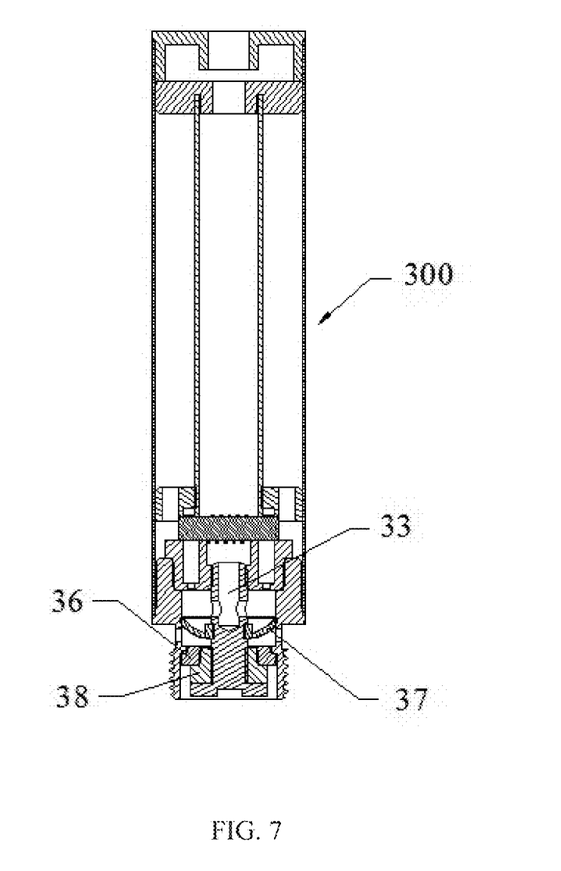
FIG. 7 is a schematic cross sectional view of an atomizing device of an electronic cigarette in accordance with a third embodiment.

Referring to FIG. 7, an atomizing device 300 in accordance with a third embodiment is provided. The atomizing device 300 is essentially similar to the atomizing device 100, however, an adjustable ring 38 is added between the insulated ring 36 and the tubular electrode 33. The adjustable ring 38 can be an elastic member, or can be made of a compressible material such as silicon dioxide. The adjustable ring 38 is configured to allow the tubular electrode 33 movable along a central axis of the atomizing device 300, thereby facilitating assembly and avoiding damage to the tubular electrode 33. In an alternative embodiment, the adjustable ring 38 can be added between the insulated ring 36 and the screw sleeve 32, and the tubular electrode 33 can be movable together with the insulated ring 36.

Figure 8:
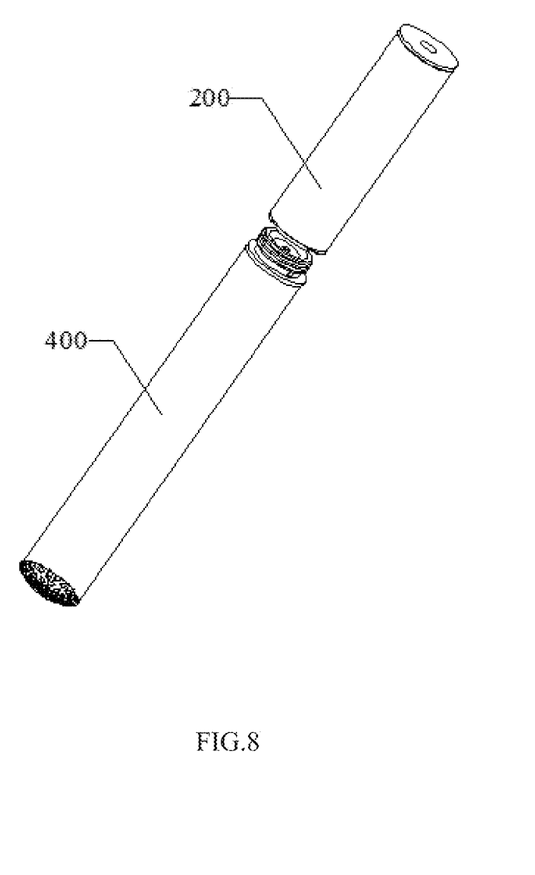
FIG. 8 is a schematic isometric view of an electronic cigarette in accordance with a fourth embodiment.

Referring to FIG. 8, an electronic cigarette in accordance with a fifth embodiment is provided. The electronic cigarette includes an atomizing device 200 and a battery assembly 400 configured to be connected to and power for the atomizing device 200.

Referring to FIG. 9, in a suction state, the flexible membrane 37 deforms, thus can act as an air valve for the atomizing device. In other states, the flexible membrane 37 contacts the tubular electrode 33 and the screw sleeve 32, thus can prevent the oil of the atomizing device from leaking out, thereby oil pollution can be avoided.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizing device of an electronic cigarette, comprising:
an atomizing sleeve;
an air pipe received in the atomizing sleeve, an annular space being formed between the air pipe and the atomizing sleeve for containing a tobacco oil;
an oil obstructing ring located at an end of the air pipe, the oil obstructing ring having an oil hole;
an atomizing assembly positioned under the oil obstructing ring, the atomizing assembly including a porous body and a heating coil wrapping around the porous body;
a screw sleeve and an electrode respectively electrically connected to two ends of the heating coil;
a flexible membrane having an inner wall attached to the electrode, and an outer wall in contact with an inner wall of the screw sleeve, the flexible membrane capable of deformable to form an air space between the outer wall of the flexible membrane and the inner wall of the screw sleeve;
an insulated ring, the electrode being located in the screw sleeve with the insulated ring located between the electrode and the screw sleeve; and
an adjustable ring positioned between the insulated ring and the electrode.

2. The atomizing device of claim 1, further comprising a support supporting the atomizing assembly, the support having two guiding holes, two ends of the heating coil extending through the guiding holes to be electrically connected to the screw sleeve and the electrode.

3. The atomizing device of claim 1, wherein the flexible membrane is in a bowl shape, and has a protrusion formed at a bottom thereof, and a through hole formed in the protrusion, the electrode extends though the through hole.

4. The atomizing device of claim 3, wherein the electrode comprises a front portion, a middle portion and a distal portion, the front portion includes a central through hole and two orifices in communication with the central through hole, the middle portion is recessed relative to both of the front portion and the distal portion, and the protrusion of the flexible membrane engages with the middle portion.

5. The atomizing device of claim 3, wherein a top air chamber and a bottom air chamber are formed in the screw sleeve by flexible membrane, and the screw sleeve comprises two orifices in communication with the bottom air chamber.

6. An atomizing device of an electronic cigarette, comprising:
an atomizing sleeve;
an air pipe received in the atomizing sleeve, an annular space being formed between the air pipe and the atomizing sleeve for containing a tobacco oil;
an oil obstructing ring located at an end of the air pipe, the oil obstructing ring having an oil hole;
an atomizing assembly positioned under the oil obstructing ring;
a screw sleeve and an electrode respectively electrically connected to the atomizing assembly;
a bowl-shaped flexible membrane having a through hole, the electrode engaging with and extending through the through hole of the flexible membrane, an edge of the flexible membrane in contact with an inner wall of the screw sleeve, the flexible membrane capable of deformable to form an air space between the edge of the flexible membrane and the inner wall of the screw sleeve;
an insulated ring, the electrode being located in the screw sleeve with the insulated ring located between the electrode and the screw sleeve; and
an adjustable ring positioned between the insulated ring and the electrode.

7. An electronic cigarette comprising an atomizing device of claim 1, and a battery assembly connected to the atomizing device.

8. The atomizing device of claim 6, wherein the flexible membrane has a protrusion formed at a bottom thereof, and the through hole is formed in the protrusion.

9. The atomizing device of claim 8, wherein the electrode comprises a front portion, a middle portion and a distal portion, the front portion includes a central through hole and two orifices in communication with the central through hole, the middle portion is recessed relative to both of the front portion and the distal portion, and the protrusion of the flexible membrane engages with the middle portion.

10. The atomizing device of claim 8, wherein a top air chamber and a bottom air chamber are formed in the screw sleeve by flexible membrane, and the screw sleeve comprises two orifices in communication with the bottom air chamber.

* * * * *